US00PP15883P2

(12) United States Plant Patent
Kobayashi

(10) Patent No.: US PP15,883 P2
(45) Date of Patent: Jul. 19, 2005

(54) *POINSETTIA* PLANT NAMED 'PER1072'

(50) Latin Name: *Euphorbia pulcherrima*
Varietal Denomination: PER1072

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 10/955,478

(22) Filed: Sep. 30, 2004

(51) Int. Cl.[7] ..... A01H 5/00
(52) U.S. Cl. ..... Plt./307
(58) Field of Search ..... Plt./307

(56) References Cited

U.S. PATENT DOCUMENTS

PP12,546 P2 * 4/2002 Fruehwirth ..... Plt./307
PP12,725 P2 * 6/2002 Fruehwirth ..... Plt./303

OTHER PUBLICATIONS

UPOV ROM GTITM Computer Database, GTI Jouve Retrieval Software 2004/05 Citation for 'PER1072'.*

* cited by examiner

*Primary Examiner*—Anne Marie Grunberg
*Assistant Examiner*—W. C. Haas
(74) *Attorney, Agent, or Firm*—C. A. Whealy

(57) ABSTRACT

A new and distinct cultivar of *Poinsettia* plant named 'PER1072', characterized by its inflorescences with recurved red-colored flower bracts; recurved dark green-colored leaves; uniform, compact, upright and mounded plant habit; early season flowering; natural season flower maturity date is mid-November for plants grown in Encinitas, Calif., and excellent post-production longevity.

1 Drawing Sheet

Bontanical designation: *Euphorbia pulcherrima* Willd.
Variety denomination: 'PER1072'.

BACKGROUND OF THE INVENTION

The present Invention relates to a new and distinct cultivar of *Poinsettia* plant, botanically known as *Euphorbia pulcherrima* Willd., and hereinafter referred to by the name 'PER1072'.

The new *Poinsettia* is a product of a planned breeding program conducted by the Inventor in Encinitas, Calif. The objective of the breeding program is to create new early flowering *Poinsettia* cultivars having strong stems, recurved leaves and flower bracts, attractive flower bract coloration, uniform plant habit and excellent post-production longevity.

The new *Poinsettia* originated from a cross-pollination made by the Inventor in December, 1999, of a proprietary selection of *Euphorbia pulcherrima* Willd. identified as code number V-82, not patented, as the female, or seed, parent, with a proprietary selection of *Euphorbia pulcherrima* Willd. identified as V-01, not patented, as the male, or pollen, parent. The cultivar PER979 was discovered and selected by the Inventor as a single flowering plant within the progeny of the stated cross-pollination in a controlled environment in Encinitas, Calif, in December, 2000.

Asexual reproduction of the new *Poinsettia* by terminal cuttings propagated in a controlled environment in Encinitas, Calif., since July, 2001, has shown that the unique features of this new *Poinsettia* are stable and reproduced true to type in successive generations of asexual reproduction.

BRIEF SUMMARY OF THE INVENTION

The following traits have been repeatedly observed and are determined to be the unique characteristics of 'PER1072'. These characteristics in combination distinguish 'PER1072' as a new and distinct cultivar:

1. Inflorescences with recurved red-colored flower bracts.
2. Recurved dark green-colored leaves.
3. Uniform, compact, upright and mounded plant habit.
4. Early season flowering; natural season flower maturity date is mid-November for plants grown in Encinitas, Calif.
5. Excellent post-production longevity.

Plants of the new *Poinsettia* differ from plants of the female parent selection primarily in flower bract color as plants of the female parent selection have bi-colored flower bracts.

Plants of the new *Poinsettia* have darker-colored leaves and flower bracts than plants of the male parent selection.

Plants of the new *Poinsettia* can be compared to plants of the cultivar Windark, disclosed in U.S. Plant Pat. No. 12,546. In side-by-side comparisons conducted in Encinitas, Calif., plants of the new *Poinsettia* differed primarily in time to flower as plants of the new *Poinsettia* flowered about two weeks earlier than plants of the cultivar Windark.

BRIEF DESCRIPTION OF THE PHOTOGRAPHS

The accompanying colored photographs illustrate the overall appearance of the new *Poinsettia,* showing the colors as true as it is reasonably possible to obtain in colored reproductions of this type. Colors in the photographs may differ slightly from the color values cited in the detailed botanical description which accurately describe the colors of the new *Poinsettia.*

The photograph at the top of the sheet comprises a side perspective view of a typical flowering plant of 'PER1072' grown in a container.

The photograph at the bottom left of the sheet is a close-up view of typical inflorescences of 'PER1072'.

The photograph at the bottom right of the sheet comprises a top perspective view of a typical plant of 'PER1072'.

DETAILED BOTANICAL DESCRIPTION

The new *Poinsettia* has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Encinitas, Calif. during the autumn and winter under commercial practice in a polyethylene-covered greenhouse with day temperatures averaging about 24° C., night temperatures averaging about 19° C. and light levels about 4,000 foot-candles. Single plants were grown in 16.5-cm pots and pinched once. Plants were flowered under natural season short day/long night conditions. Plants were about 15 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar PER1072.

Parentage:

*Female parent.*—Proprietary selection of *Euphorbia pulcherrima* Willd. identified as code number V-82, not patented.

*Male parent.*—Proprietary selection of *Euphorbia pulcherrima* Willd. identified as code number V-01, not patented.

Propagation:

*Type cutting.*—Terminal cuttings.

*Time to initiate roots.*—About 10 days at 20 to 22° C.

*Time to develop roots.*—About 28 days at 20 to 22° C.

*Root description.*—Thick, fibrous, freely-branching; white in color.

Plant description:

*Plant form.*—Narrow inverted triangle; top of plant mounded.

*Growth habit.*—Upright, compact and uniform plant habit. Moderately vigorous.

*Plant height.*—About 28 cm.

*Plant diameter or spread.*—About 24 cm.

*Lateral branch description.*—Quantity: About eight lateral branches develop after pinching. Length: About 20 cm. Diameter: About 6 mm. Internode length: About 2.6 cm. Strength: Strong. Texture: Smooth; glabrous. Color: 146B.

*Foliage description.*—Arrangement: Alternate, single. Length: About 8 cm. Width: About 7.5 cm. Shape: Elliptic. Apex: Acuminate. Base: Obtuse. Margin: Entire with irregular lobing. Venation pattern: Pinnate. Texture, upper and lower surfaces: Glabrous, smooth. Surface: Rugose. Aspect: Recurved. Color: Developing foliage, upper surface: 147A. Developing foliage, lower surface: 147B. Fully expanded foliage, upper surface: Darker than 147A. Fully expanded foliage, lower surface: 147B. Venation, upper surface: 147B. Venation, lower surface: 147D. Petiole: Length: About 1.8 cm. Diameter: About 3 mm. Texture, upper and lower surfaces: Smooth; glabrous. Color: 182A.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent.

*Natural flowering season.*—Autumn/winter in Northern Hemisphere. Flower initiation and development is induced under long nyctoperiod conditions. Early season flowering, response time, about 7.5 weeks; natural season flower maturity date is mid-November for plants grown in Encinitas, Calif.

*Post-production longevity.*—Plants of the new *Poinsettia* maintain good substance and bract color for about four weeks under interior conditions.

*Inflorescence size.*—Diameter: About 10.5 cm. Height (depth): About 5 cm.

*Flower bracts.*—Quantity per inflorescence: About 20. Length, largest bracts: About 5.5 cm. Width, largest bracts: About 6.3 cm. Shape: Elliptic. Apex: Acuminate. Base: Obtuse. Margin: Entire with irregular lobing. Texture, upper and lower surfaces: Glabrous; velvety. Surface: Rugose. Aspect: Recurved. Venation pattern: Pinnate. Color: Developing or transitional bracts, upper surface: 53A. Developing or transitional bracts, lower surface: 53B. Fully developed bracts, upper surface: 53B; color does not fade with development. Fully developed bracts, lower surface: 53C. Venation, upper and lower surfaces: Similar to flower bract color. Bract petiole: Length: About 1.5 cm. Diameter: About 3 mm. Texture, upper and lower surfaces: Smooth; glabrous. Color: 187B.

*Cyathia.*—Quantity per corymb: About 14. Diameter of cyathia cluster: About 2.3 cm. Length: About 1 cm. Width: About 6 mm. Shape: Ovoid. Color, immature: 146B. Color, mature: 146B. Peduncle: Length: About 3 mm. Diameter: About 2 mm. Strength: Strong. Aspect: Mostly upright. Texture: Smooth; glabrous. Color: 145A. Stamens: Quantity per cyathium: About ten. Anther shape: Bi-lobed. Anther length: About 1 mm. Anther color: 46A. Amount of pollen: Scarce. Pollen color: 13A. Pistils: None observed. Nectaries: Quantity per cyathium: About one or two. Size: About 3 mm by 4 mm. Color: 21A.

Disease/pest resistance: Resistance to pathogens and pests common to *Poinsettias* has not been observed on plants grown under commercial conditions.

It is claimed:

1. A new and distinct cultivar of *Poinsettia* plant named 'PER1072', as illustrated and described.

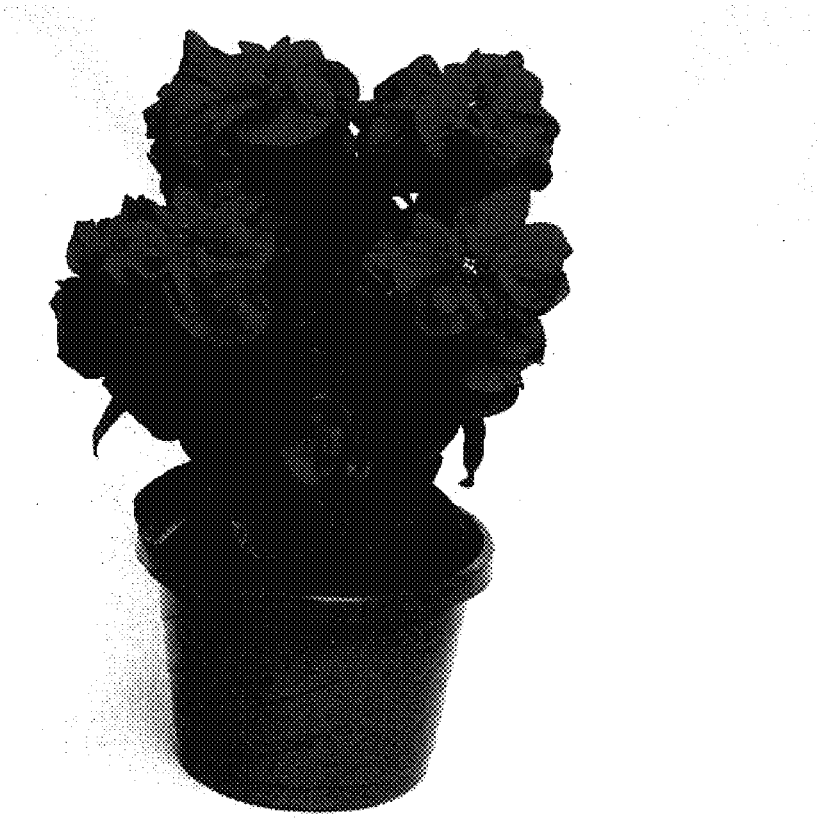
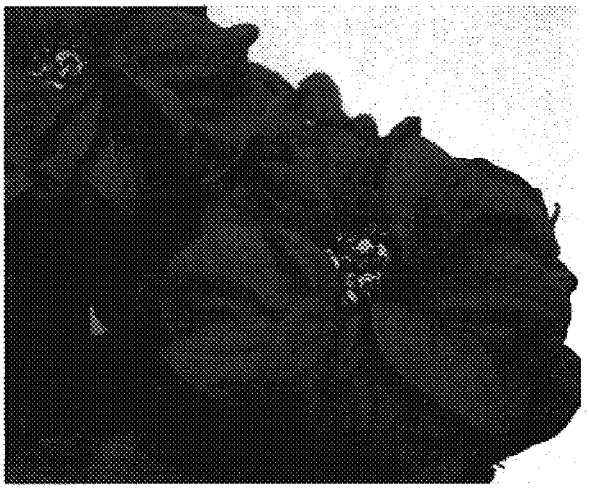
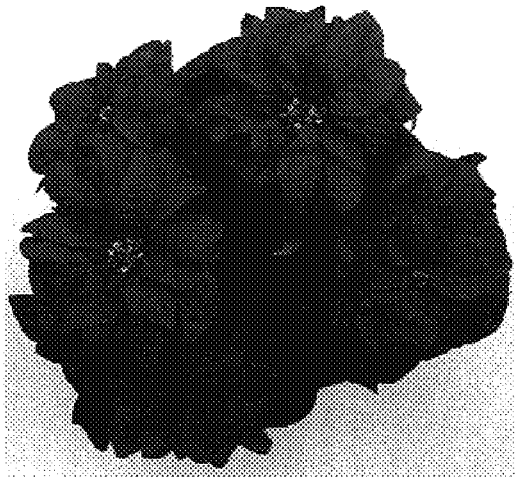

* * * * *